United States Patent [19]
Petty et al.

[11] 4,291,704
[45] Sep. 29, 1981

[54] SPIROMETER DEVICE

[75] Inventors: Thomas L. Petty; Balinderjeet S. Baidwan, both of Denver, Colo.

[73] Assignee: Dale E. Braddy, Oak Row Village, Ill.

[21] Appl. No.: 103,237

[22] Filed: Dec. 13, 1979

[51] Int. Cl.³ .............................................. A61B 5/08
[52] U.S. Cl. .................... 128/728; 272/99; 46/88
[58] Field of Search ................ 128/725–730; 272/99; 46/88

[56] References Cited

U.S. PATENT DOCUMENTS

| | | | |
|---|---|---|---|
| 225,710 | 3/1880 | Marsh | 128/728 |
| 1,781,735 | 11/1930 | Scott | 128/728 |
| 3,066,440 | 12/1962 | Van Dam | 46/88 |
| 3,321,976 | 5/1967 | Jones | 128/730 |
| 3,333,844 | 8/1967 | Jurschak | 128/728 X |
| 3,343,529 | 9/1967 | Miller et al. | 128/729 |
| 3,507,271 | 4/1970 | Reiner | 128/728 |
| 3,810,461 | 5/1974 | McCormick | 272/99 X |
| 3,826,247 | 7/1974 | Ruskin et al. | 128/727 |
| 4,158,360 | 6/1979 | Adams | 128/725 |

FOREIGN PATENT DOCUMENTS 148974  11/1952  Australia .................................. 46/88

Primary Examiner—Kyle L. Howell
Attorney, Agent, or Firm—Gary M. Polumbus

[57] ABSTRACT

A spirometer device includes an open ended inflatable elastomeric vessel with calibrated indicia along its length for indicating the volume of gas contained in the vessel and a mouth piece consisting of two relatively rotatable sections, one of said sections being connected to the open end of the vessel so that air can be blown through the mouth piece to inflate the vessel. The mouth piece contains a unique valving system and an air actuated sound generating device so that depending upon the relative angular relationship of the two sections, air can be blown into the vessel and retained in the vessel or allowed to escape from the vessel either through the sound generating device or not.

4 Claims, 5 Drawing Figures

U.S. Patent   Sep. 29, 1981   4,291,704
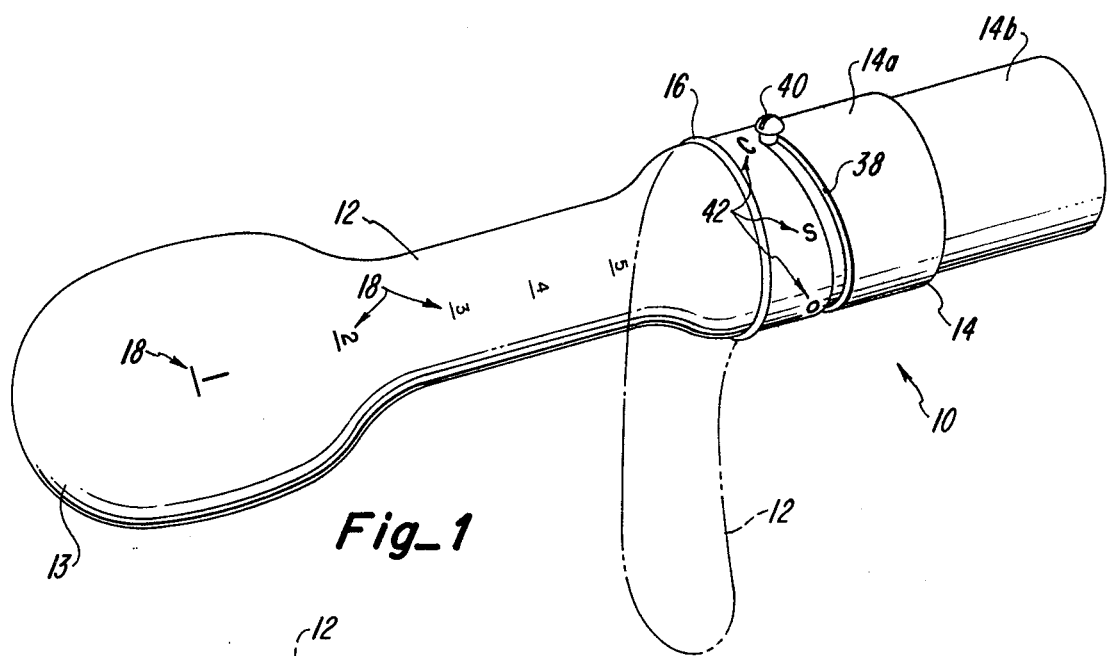
Fig_1
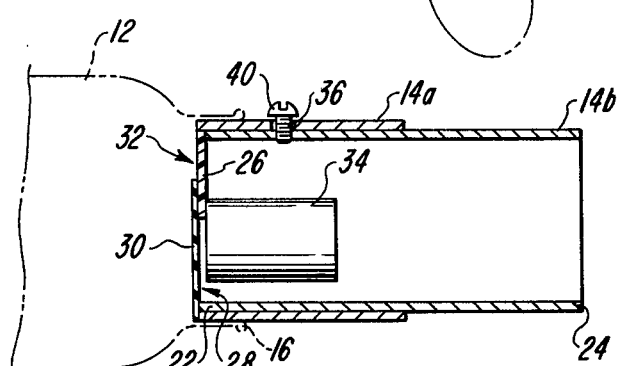
Fig_2
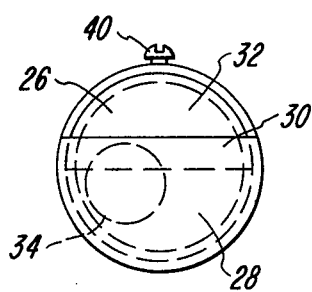
Fig_3
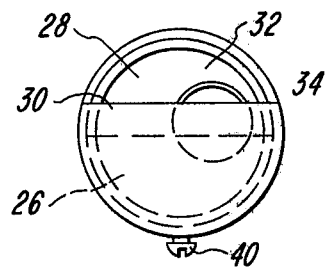
Fig_4
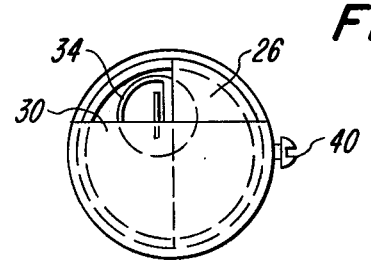
Fig_5

SPIROMETER DEVICE

BACKGROUND OF THE INVENTION

Numerous spirometer devices have been developed through the years for measuring the lung capacity of a human being. Most of these devices are fairly sophisticated and for doctors use so that an accurate measure of the lung air capacity can be determined merely by having the individual blow air from his lungs into the device after having taken a deep breath.

One drawback with most prior art spirometer devices is that they are relatively expensive to manufacture and for that reason are not generally suitable for home use by the consuming public.

Examples of prior art spirometer devices are disclosed in U.S. Pat. Nos. 3,507,271 issued to E. W. Reiner, 1,781,735 issued to R. W. Scott, 3,826,247 issued to Ruskin, et al, and 3,343,529 issued to R. A. Miller, et al.

SUMMARY OF THE INVENTION

The spirometer device of the present invention was designed and developed to provide a reasonably accurate measure of the lung capacity of an individual at a price affordable by most consumers so that the device could be utilized in the home without a doctor's assistance.

The spirometer device includes an inflatable elastomeric vessel having calibrated indicia on an external surface thereof and an open end adapted to be connected in fluid communication with a mouth piece or main body. The main body has two component sections which are rotatably connected relative to each other so that a valve contained in the main body can be placed in one of three positions by relative rotation of the main body sections.

The valve includes a partition extending across the interior of one of the main body sections and a flexible membrane extending across the interior of the other of the main body sections in adjacent relationship to the partition. The partition has a hole therethrough which can be aligned with an opening in the membrane to allow air to be directed into and out of the vessel. An air actuated sound generating device is positioned across a portion of the hole in the partition so that air passing through the opening in the membrane can either be passed through the sound generating device or through a portion of the hole not covered by the sound generating device depending upon whether or not it is desirable to generate a noise by the released air.

The spirometer device is operated by aligning the hole in the partition with the opening through the membrane and blowing air into the vessel after the lungs have been fully inflated so that virtually all of the air in the individual's lungs is directed into the vessel. After the air is in the vessel, the body sections of the mouth piece are rotated relative to each other so that the hole and the opening are misaligned to prevent air from escaping from the vessel. The vessel is designed so that it will initially expand radially at its distal end and will continue to so expand in an inward direction toward the mouth piece. In this manner, by use of the calibrated indicia on the exterior surface of the vessel, the volume of air directed into the vessel can be closely approximated by the extent to which the vessel has been inflated. After the volume of air in the balloon has been determined, the hole and opening in the partition and membrane respectively, are aligned so that the air will escape from the vessel, either through or alongside the sound generating element as desired, until all air is released from the vessel leaving the device in a condition for reuse.

BRIEF DESCRIPTION OF THE DRAWINGS

FIG. 1 is a perspective view of the spirometer device of the present invention in a partially inflated state with the vessel in a noninflated state illustrated in phantom lines.

FIG. 2 is a longitudinal section taken through the mouth piece of the device illustrated in FIG. 1 with a fragmented portion of the vessel of the device illustrated in phantom lines.

FIG. 3 is an end view of the leading end of the mouth piece with the mouth piece sections being oriented in a closed position.

FIG. 4 is an end view similar to FIG. 3 with the mouth piece section being oriented in an open position.

FIG. 5 is an end view similar to FIGS. 3 and 4 with the mouth piece sections being oriented in a sound generating position.

DESCRIPTION OF THE PREFERRED EMBODIMENT

The spirometer device 10 of the present invention includes two basic component parts, an elongated, inflatable elastomeric vessel 12 and a mouth piece or main body 14. The vessel 12 and main body 14 are interconnected in fluid communication so that an individual using the device can blow air from his lungs through the main body and into the vessel to inflate the vessel with a volume of air closely approximating the air capacity of the individual's lungs.

The vessel 12 is elongated in configuration and has one open end 16 adapted to fit onto the main body 14 in a manner which will be described later. The vessel has externally located calibrated indicia 18 along its length adapted to indicate the volume of air in the vessel at any particular time. For example, the indicia 18 could represent a number of liters of air in the vessel at any given time. The vessel naturally inflates from its distal end 13 inwardly toward its connection to the main body at the open end 16 of the vessel. Accordingly, the calibrated indicia indicating the volume of air in the vessel would increase in value from the distal end 13 toward the open end 16 of the vessel. The volume of air in the vessel is determined by locating the position at which the vessel becomes enlarged relative to the remainder of the vessel and determining the volume of such air by referring to the calibrated indicia on the vessel at that location. For example, the device as illustrated in FIG. 1 indicates that approximately 2 liters of air are in the vessel.

The mouth piece or main body 14 includes two cylindrical sections, an outer section 14a and an inner section 14b, with the outer section being approximately half the length of the inner section and being positioned rotatably about the inner section at a leading end 22 thereof. Each section 14a and 14b is approximately one inch in diameter so that a trailing end 24 of the inner section 14b can be inserted into one's mouth to allow air to be directed through the main body into the vessel 12 attached to the main body.

As will be appreciated by reference to FIGS. 1 and 2, the vessel 12 is attached to the main body 14 by stretching the open end 16 of the vessel and placing it around the leading end of the outer section 14a so that the vessel will remain secured to the main body through its frictional engagement with the outer section.

The inner section 14b of the main body 14 has a transversely extending semi-circular rigid partition 26 securely positioned in the leading open end 22 thereof so as to define a semi-circular hole 28 at the leading end of the inner section. Similarly, the outer section 14a has a transversely extending flexible membrane 30 secured in its leading open end which is slightly greater than semi-circular in configuration. This flexible membrane 30 may be made of a soft rubber material which is capable of forming an hermetic seal with the rigid partition 26 in the inner section which can be made of plastic. The membrane defines an opening 32 through the leading end of the outer section which approaches a semi-circular configuration that is slightly smaller. With this arrangement, the inner and outer sections 14b and 14a respectively can be rotated relative to each other so that the partition 26 and membrane 30 are in alignment (FIG. 4) thereby aligning the hole 28 in the inner element with the opening 32 through the outer element so that air can pass freely through the main body 14 into the vessel 12. Alternately, the two main body sections can be rotated approximately 180° from the aforedescribed position into the position illustrated in FIGS. 2 and 3 so that the hole 28 in the inner element 14b is covered by the membrane 30 and the opening 32 in the outer element 14a is covered by the partition 26 thereby blocking the passage of air past the leading ends of the two main body sections. Of course, the flexible nature of the membrane allows it to form an hermetic seal with the partition. It is important to note that the membrane 30 on the outer section is situated on the vessel side of the partition 26 so that when the air pressure in the vessel is greater than the air pressure in the main body, the air pressure will hold the membrane against the partition in an hermetic sealing relationship to prevent the escape of air from the vessel.

An air actuatable sound generating element 34 is affixed to the internal surface of the inner section 14b at the leading end 22 thereof so as to be in axial alignment with a portion of the hole 28 at the leading end of the inner section. The sound generating element 34 in the disclosed embodiment is cylindrical in configuration having an opening at each end thereof with a reed, not seen, extending axially and internally thereof so that air passing through the element will cause the reed to vibrate emitting an audible sound indicative of the flow of air from the vessel 12 through the main body 14.

It will be appreciated that the inner and outer sections 14b and 14a of the mouth piece or main body 14 can be positioned in one of three significant relationships illustrated in FIGS. 3, 4 and 5. One of these relationships (FIG. 4), which will be referred to as an open position, aligns the hole 28 in the inner element 14b with the opening 32 in the outer element 14a so that air can be blown through the mouth piece into the vessel to inflate same and also released from the vessel for a reverse flow through the mouth piece. In this position only a small amount of air would pass through the sound generating element 34 and thus no sound would be generated thereby. The second position (FIG. 3), which will be referred to as a closed position, aligns the partition 26 in the inner element 14b with the opening 32 through the outer element 14a and the membrane 30 in the outer element with the hole 28 in the inner element so that air is not allowed to pass from the vessel through the main body of the device. In the third position (FIG. 5), which will be referred to as a sound generating position, the opening 32 in the outer section is aligned with the sound generating element 34 in the inner section so that air in the vessel will be released almost entirely through the sound generating element which would audibly indicate the release of such air.

In the preferred embodiment, a slot 38 of substantially semi-circular configuration is provided in the outer section 14a of the main body 14 and a guide 40 is extended through the slot from the outside of the main body and affixed to the inner section 14b to retain a desired longitudinal relationship of the inner and outer sections regardless of their angular relationship. Accordingly, when the inner and outer sections are relatively pivoted about the longitudinal axes thereof, the guide 40 rides in the slot 38 to maintain the desired longitudinal relationship of the two sections. As will be appreciated, the slot is formed at a slight angle to a transverse plane through the main body sections so that when the sections are moved into the closed position (FIGS. 2 and 3) blocking the escape of air from the vessel, the sections are actually displaced axially relative to their positions in the open position (FIG. 4) to press the membrane 30 against the partition 26 to form a more effective seal. Alternatively, when the sections are rotated into their open position wherein air is allowed to be released from the vessel into and through the main body, the sections are displaced axially in the opposite direction a slight amount. Indicia 42 is provided on the outer section of the main body alongside the slot 38 to indicate the relative angular relationship of the inner and outer sections so that the user of the device can tell visually whether the device is in the open, closed or sound generating position described hereinbefore.

In operating the device, the inner and outer sections 14b and 14a are rotated relative to each other into the open position (FIG. 4). The user then takes a deep breath and exhales all of the air from his lungs through the main body and into the vessel 12 to inflate same. At the completion of this exhalation, the inner and outer sections are rotated relative to each other so that the guide 40 indicates, via the indicia 42, that the sections are in the closed position (FIG. 3) to seal the air in the vessel. The volume of air in the vessel is then determined by locating the position at which the vessel becomes enlarged relative to the remainder of the vessel and reading the volume of air in the vessel off the calibrated information 18 along the length of the vessel. The air is then released from the vessel by rotating the sections at the main body either into the open position or the sound generating position so as to allow the air in the vessel to escape through the main body.

Although the invention has been described in considerable detail, it will be understood that variations and modifications can be made within the spirit and scope of the invention.

What I claim is:
1. A spirometer device comprising, in combination:
an inflatable elastomeric vessel having one open end and calibration indicia for indicating the volume of air contained in the vessel, and
a main body releasably attached to said vessel at said open end in fluid communication with the interior of said vessel, said main body having two relatively rotatable sections of generally hollow tubular construction, one of said sections having a partition with a hole therethrough wherein said partition extends generally transversely of said tubular main body, the other of said sections having a flexible sealing membrane with an opening therethrough positioned adjacent and parallel to said partition on the vessel side of said partition, so that said membrane can be rotated relative to said partition to selectively align the misalign said hole and said opening, whereby when said hole and opening are aligned, air can be directed through said main body into said vessel, and, when the hole and opening are misaligned, air can be sealed in said vessel, said main body further including an air actuated, audible sound generating element secured therein in alignment with at least a portion of said hole in the partition so that air escaping from said vessel through said hole can be directed through said element to produce an audible sound.

2. The device of claim 1 wherein said sound generating element is smaller than said hole in the partition so that air escaping from said vessel through said opening in the membrane can be directed solely through the hole in the partition in one relationship of the two body sections and through the hole and the sound generating element in another relationship of the two body sections.

3. The device of claim 1 wherein one of said body sections is positioned at least partially within the other of said body sections and wherein said other body section has a slot therethrough in alignment with a portion of said one body section, said one body section having a protrusion adapted to slide within said slot upon relative rotational movement of said body sections.

4. The device of claim 3 wherein said other body section has indicia adjacent to said slot indicating the relationship of said body sections.

* * * * *